US00PP22769P3

(12) United States Plant Patent
Egger

(10) Patent No.: US PP22,769 P3
(45) Date of Patent: Jun. 5, 2012

(54) ***EUCOMIS* PLANT NAMED 'FRECKLES'**

(50) Latin Name: ***Eucomis* spp.**
Varietal Denomination: Freckles

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 134 days.

(21) Appl. No.: 12/806,935

(22) Filed: Aug. 23, 2010

(65) Prior Publication Data

US 2012/0047612 P1 Feb. 23, 2012

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Susan McCormick Ewoldt
(74) *Attorney, Agent, or Firm* — Klarquist Sparkman, LLP

(57) ABSTRACT

A new and distinct *Eucomis* plant characterized by its vigor, extremely well spotted leaves on top and bottom sides, multiple crowns, and leaf margins that are wavy.

1 Drawing Sheet

Botanical denomination: *Eucomis* spp.
Variety designation: Freckles.

BACKGROUND OF THE INVENTION

The present invention relates to a new and distinct *Eucomis,* and given the cultivar name is 'Freckles'. *Eucomis* is in the family Hyacinthaceae. 'Freckles' is a hybrid resulting from a planned breeding program to produce interesting foliage *Eucomis.* The cross was made using *Eucomis* 'Leia' (an unpatented plant), as the seed parent, and *Eucomis vandermerwei,* as the pollen parent. It was selected for best habit, color, and crown count from many seedlings of the cross in Canby, Oreg.

Compared to *Eucomis* 'Leia' (an unpatented plant), the seed parent, the new variety has extremely well spotted leaves versus faintly spotted leaves. Both have high crown count. The flowers of 'Freckles' are dark rose rather than pink.

Compared to *Eucomis vandermerwei,* the pollen parent, the new variety is much larger and more vigorous with larger leaves and flowers. The new variety multiplies much more quickly.

Compared the *Eucomis vandermerwei* 'Octopus' (an unpatented plant), the new variety 'Freckles' is larger, more vigorous, with broader and more upright leaves, and with more and larger flowers.

SUMMARY OF THE INVENTION

The new variety is unique with its vigor, extremely well spotted leaves on top and bottom sides, multiple crowns, and leaf margins that are wavy.

This new cultivar has been reproduced only by asexual propagation (division, tissue culture). Each of the progeny exhibits identical characteristics to the new cultivar. Asexual propagation by leaf cuttings, tissue culture, and division using standard techniques as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a 2-year-old plant in of *Eucomis* 'Freckles' in a one gallon container in Canby, Oreg.

FIG. 2 shows a close up of the flowers of the new variety.

DETAILED PLANT DESCRIPTION

The following is a detailed description of the new *Eucomis* cultivar based on observations 4" pot size, nine month old specimens grown from tissue culture, grown in the greenhouse in Canby, Oreg. The color descriptions are all based on The Royal Horticultural Society Colour Chart, 5$^{th}$ edition.

Plant:
- *Type.*—Bulbous herbaceous perennial.
- *Hardiness.*—USDA Zones 7 to 10.
- *Size.*—Grows to 39 cm wide and 29 cm tall from the top of the soil to the top of the foliage.
- *Form.*—Clumping.

Leaf:
- *Type.*—Simple.
- *Shape.*—Strap-shaped.
- *Arrangement.*—Basal rosette.
- *Blade size.*—Grows to 32 cm long and 4 cm wide.
- *Margins.*—Entire and undulate.
- *Apex.*—Acute.
- *Base.*—Clasping.
- *Surface texture.*—Glabrous on both surfaces.
- *Venation.*—Parallel.
- *Color.*—Topside Green N137C with spots Greyed Purple N187A; bottom side Green N137A thickly spotted Greyed Purple N187A.

Inflorescence:
- *Type.*—Raceme crowned with leafy bracts.
- *Number of flowers per raceme.*—About 50.
- *Inflorescence.*—9 cm long and 4 cm wide.

*Peduncle description.*—Grows to 14 cm long and 1 cm wide, glabrous, densely spotted to almost entirely colored Greyed Purple N 187A, and topped with a coma of about 16 leafy bracts, lanceolate, entire, acuminate, 29 mm long and 9 mm wide, top and bottom side Green N137C with spots Greyed Purple N187A.

*Pedicle description.*—7 mm long and 1 mm wide, glabrous, White NN155B spotted Greyed Purple 187B.

*Bloom time.*—September to October in Canby, Oreg.

*Lastingness.*—An inflorescence lasts for 2 to 4 weeks depending on the temperatures.

Flower bud:

*Size.*—8 mm long and 5 mm wide.

*Shape.*—Oblong.

*Surface texture.*—Glabrous.

*Color.*—Greyed Purple 187A.

Flower:

*Type.*—Actinomorphic, down facing, with segments free.

*Shape.*—Stellate.

*Size.*—Grows to 19 mm wide and 11 mm deep.

*Texture.*—Waxy.

*Surface texture.*—Glabrous inside and outside.

*Color.*—Inside, Yellow Green 145C heavily tinted Greyed Purple 187C especially toward the base and edges; outside, Greyed Purple 187B.

*Corolla description.*—6 tepals, oblong, entire, acute, glabrous on both sides, 11 mm long and 3.5 mm wide.

*Pistil description.*—9 mm long, ovary 5 mm long 4 mm wide and White N155D, style 4 mm long, Red Purple 62D, stigma Greyed Purple 186C.

*Stamen.*—6, 6 mm long, filaments 5 mm long, 2 mm wide at the base, and Yellow Green 145A, anthers 1 mm long and Green Yellow 1C, pollen Yellow 11B.

*Fragrance.*—Light.

Fruit:

*Type.*—3 segmented capsule.

*Size.*—11 mm long, 10 mm wide.

*Shape.*—Broad.

*Color.*—Greyed Purple 187A.

Seed:

*Number.*—0 to 2 per capsule.

*Size.*—3 mm long and 1.5 mm wide.

*Shape.*—Oval.

*Color.*—Black 202A.

Pest and diseases: Pests and diseases are infrequent on *Eucomis* spp. No problems have been observed on this plant grown under commercial conditions in Canby, Oreg.

I claim:

1. A new and distinct *Eucomis* plant as herein shown and described.

* * * * *

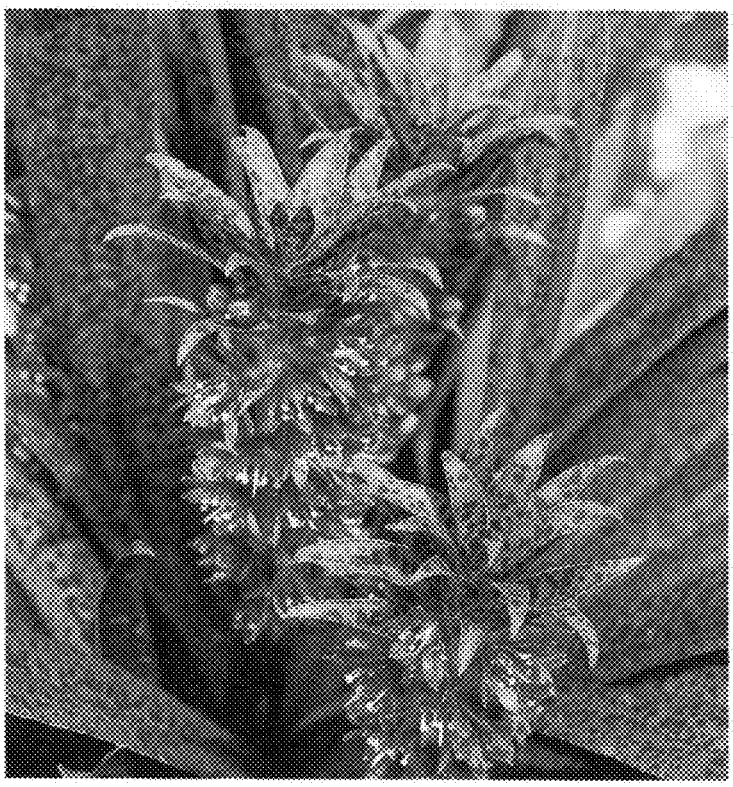

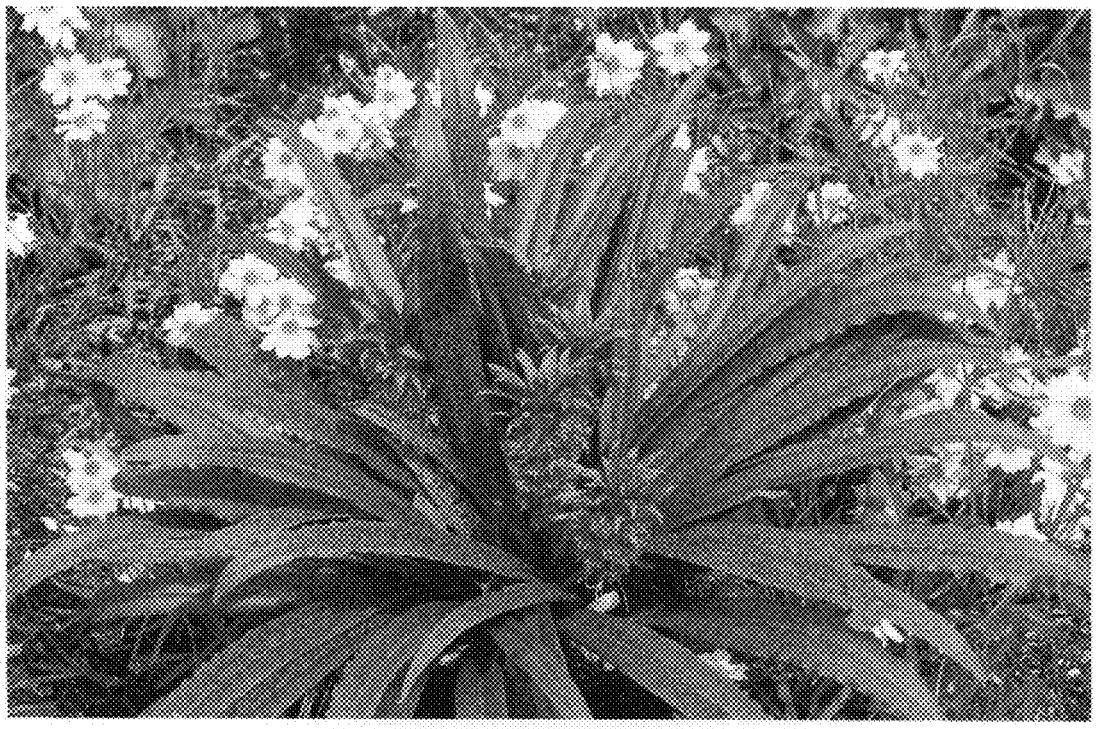
Figure 1 above. Figure 2 below.